US006929009B2

(12) United States Patent
Makower et al.

(10) Patent No.: US 6,929,009 B2
(45) Date of Patent: *Aug. 16, 2005

(54) METHOD AND APPARATUS FOR TRANSMYOCARDIAL DIRECT CORONARY REVASCULARIZATION

(75) Inventors: Joshua Makower, Los Altos, CA (US); J. Christopher Flaherty, Los Altos, CA (US); Timothy R. Machold, Moss Beach, CA (US); Jason Brian Whitt, San Francisco, CA (US); Margaret W. Tumas, Orinda, CA (US); Theodore C. Lamson, Pleasanton, CA (US); Marc Jensen, Los Gatos, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 10/150,306

(22) Filed: May 16, 2002

(65) Prior Publication Data

US 2002/0179098 A1 Dec. 5, 2002

Related U.S. Application Data

(63) Continuation of application No. 09/994,222, filed on Nov. 26, 2001, which is a continuation of application No. 09/710,332, filed on Nov. 9, 2000, which is a continuation of application No. 09/059,531, filed on Apr. 13, 1998, now abandoned, which is a continuation-in-part of application No. 08/837,295, filed on Apr. 11, 1997, now abandoned.
(60) Provisional application No. 60/028,922, filed on Aug. 26, 1996.

(51) Int. Cl.[7] .............................................. A61B 19/00
(52) U.S. Cl. ...................................... 128/898; 606/108
(58) Field of Search ............................. 128/898; 606/1, 606/108, 167, 170–171; 604/7, 8

(56) References Cited

U.S. PATENT DOCUMENTS

| 3,995,617 A | 12/1976 | Watkins et al. ................. 128/1 |
| 4,546,499 A | 10/1985 | Possis et al. ................... 623/1 |

(Continued)

FOREIGN PATENT DOCUMENTS

| EP | 335205 | 1/1985 | |
| EP | 230996 | 1/1987 | .......... A61M/25/00 |
| WO | 9516476 | 6/1995 | |

(Continued)

OTHER PUBLICATIONS

MS Hochberg, AJ Roberts, V Parsonnet, D Fisch; Selective arterialization of coronary veins: Clinical experience of 55 American heart surgeons; pp. 195–201.

(Continued)

Primary Examiner—David Isabella (57) ABSTRACT

Methods and apparatus for direct coronary revascularization wherein a transmyocardial passageway is formed between a chamber of the heart and a coronary blood vessel to permit blood to flow therebetween. In some embodiments, the transmyocardial passageway is formed between a chamber of the heart and a coronary vein. The invention includes unstented transmyocardial passageways, as well as transmyocardial passageways wherein protrusive stent devices extend from the transmyocardial passageway into an adjacent coronary vessel or chamber of the heart. The apparatus of the present invention include protrusive stent devices for stenting of transmyocardial passageways, intraluminal valving devices for valving of transmyocardial passageways, intracardiac valving devices for valving of transmyocardial passageways, endogenous tissue valves for valving of transmyocardial passageways, and ancillary apparatus for use in conjunction therewith.

28 Claims, 5 Drawing Sheets

U.S. PATENT DOCUMENTS

| | | | |
|---|---|---|---|
| 4,580,568 A | 4/1986 | Gianturco | 128/345 |
| 4,769,031 A | 9/1988 | McGough et al. | 623/1 |
| 4,850,969 A | 7/1989 | Jackson | 604/96 |
| 4,865,581 A | 9/1989 | Lundquist et al. | 600/18 |
| 4,887,608 A | 12/1989 | Mohl et al. | 128/673 |
| 4,917,667 A | 4/1990 | Jackson | 604/96 |
| 4,927,412 A | 5/1990 | Menasche | 604/96 |
| 4,934,996 A | 6/1990 | Mohl et al. | 600/17 |
| 4,969,470 A | 11/1990 | Mohl et al. | 128/673 |
| 5,011,468 A | 4/1991 | Lundquist et al. | 600/18 |
| 5,024,668 A | 6/1991 | Peters et al. | 606/194 |
| 5,033,998 A | 7/1991 | Corday et al. | 600/18 |
| 5,059,167 A | 10/1991 | Lundquist et al. | 600/17 |
| 5,106,386 A | 4/1992 | Isner et al. | 606/15 |
| 5,287,861 A * | 2/1994 | Wilk | 128/898 |
| 5,382,261 A | 1/1995 | Palmaz | 606/158 |
| 5,389,096 A | 2/1995 | Aita et al. | 606/15 |
| 5,409,019 A | 4/1995 | Wilk | 128/898 |
| 5,411,552 A | 5/1995 | Andersen et al. | 623/2 |
| 5,429,144 A | 7/1995 | Wilk | 128/898 |
| 5,443,497 A | 8/1995 | Venbrux | 623/1 |
| 5,500,014 A | 3/1996 | Quijano et al. | 623/2 |
| 5,533,957 A | 7/1996 | Aldea | 600/16 |
| 5,597,377 A | 1/1997 | Aldea | 600/16 |
| 5,607,418 A | 3/1997 | Arzbaecher | 604/891.1 |
| 5,607,465 A | 3/1997 | Camilli | 623/1 |
| 5,618,270 A | 4/1997 | Orejola | 604/164 |
| 5,626,599 A | 5/1997 | Bourne et al. | 606/194 |
| 5,643,195 A | 7/1997 | Drevet et al. | 604/9 |
| 5,655,548 A * | 8/1997 | Nelson et al. | 128/898 |
| 5,662,124 A | 9/1997 | Wilk | 128/898 |
| 5,662,711 A | 9/1997 | Douglas | 623/12 |
| 5,702,421 A | 12/1997 | Schneidt | 606/213 |
| 5,755,682 A | 5/1998 | Knudson et al. | 604/8 |
| 5,755,779 A | 5/1998 | Horiguchi | 623/1 |
| 5,800,525 A | 9/1998 | Bachinski et al. | 623/1 |
| 5,810,836 A | 9/1998 | Hussein et al. | 606/108 |
| 5,824,071 A | 10/1998 | Nelson et al. | 623/3 |
| 5,827,315 A | 10/1998 | Yoon | 606/185 |
| 5,860,951 A | 1/1999 | Eggers et al. | 604/49 |
| 6,124,523 A * | 9/2000 | Banas et al. | 623/1.15 |
| 6,196,230 B1 * | 3/2001 | Hall et al. | 128/898 |
| 6,290,728 B1 * | 9/2001 | Phelps et al. | 623/23.7 |

FOREIGN PATENT DOCUMENTS

| | | | |
|---|---|---|---|
| WO | 9632153 | 10/1996 | |
| WO | 9632971 | 10/1996 | |
| WO | 9718768 | 5/1997 | |
| WO | 9729803 | 8/1997 | |
| WO | 9806356 | 2/1998 | |
| WO | 9810714 | 3/1998 | A61F/2/06 |
| WO | 9819625 | 5/1998 | |
| WO | 9838939 | 9/1998 | |
| WO | 9838941 | 9/1998 | |
| WO | 9838942 | 9/1998 | |

OTHER PUBLICATIONS

S. Meerbaum, The promise and limitations of coronary venous retroperfusion: lessons from the past and new directions; pp 40–60.

W. Mohl; The development and rationale of pressure–controlled intermittent coronary sinus occlusion; pp 20–25.

Roberto V Haendchen, Eliot Corday; Coronary sinus interventions: State of the art and initial clinical experience with retroperfusion support during angioplasty; May 1990; pp 293–305

Ronald F Bellamy, Howard S Lowensohn, Walter Ehrlich, Robert W Baer, Effect of coronary sinus occlusion on coronary pressure–flow relations; pp H57–H64.

Andrew Zalewski, Sheldon Goldberg, Sonya Slysh, peter R Maroko; Myocardial protection via coronary sinus interventions: superior effects of arterialization compared with intermittent occlusion; 1985; pp 1215–1223.

Geroge A Pantely, J David Bristow, Herbert D Ladley, Cheryl G Anselone; Effect of coronary sinus occlusion on coronary flow, resistance, and zero flow pressure during maximum vasodilatation in swine; 1988; pp 79–86.

Wolfgang Schreiner, Friederike Neumann, Werner Mohl; The role of intramyocardial pressure during coronary sinus interventions; Oct. 1990; pp 956–967.

Alice k Jacobs, David P Faxon, William D Coats, W Mark Vogel, Thomas J Ryan; Coronary sinus occlusion: Effect on ischemic left ventricular dysfunction and reactive hyperemia; Feb. 1991; pp 442–449.

Alezandros C kralios; Fred L Anderson, Fany A Kralios; Protective effect of coronary sinus obstruction from primary ischemia–induced ventricular fibrillation in the dog; Apr. 1993; pp 987–995.

Harold L Lazar, Constance K Haan, Ximing Yang, Samuel Rivers, Sheilah Bernard, Richard J Shemin; Reduction of infarct size with coronary venous retroperfusion; Nov. 1992; Suppl. II.

Denton A Cooley, O H Frazier, Kamuran A Kadipasaoglu, Matthias J Lindenmeir, Seckin Pehlivanoglu, Jeffrey W Kolff, Susan Wilansky, Warren H Moore; Transmyocardial laser revascularization: Clinical experience with twelve month follow up 1996; 791–799.

C. Massimo, I Boffl; Myocardia resvasularization by a new method of carrying blood directly from the left ventricular cavity into the coronary circulation; Aug. 1957; 257–264.

Bennetti, F et al.; Direct myocardial revascularization without extracorporeal circulation: Experience in 700. patients; 1991; pp 312–316.

* cited by examiner

METHOD AND APPARATUS FOR TRANSMYOCARDIAL DIRECT CORONARY REVASCULARIZATION

RELATED APPLICATION

This application is a continuation of Ser. No. 09/994,222 filed on Nov. 26, 2001 which is a continuation of 09/710,332 filed on Nov. 9, 2000 which was a continuation of Ser. No. 09/059,531 filed on Apr. 13, 1998 now abandoned which was a continuation in part of Ser. No. 08/837,295 filed on Apr. 11, 1997 now abandoned which claimed priority to Provisional Application 60/028,922 filed on Aug. 26, 1996.

FIELD OF THE INVENTION

The present invention pertains generally to Medical treatment methods and devices, and more particularly to methods and devices for transluminal direct coronary revascularization.

BACKGROUND OF THE INVENTION

Coronary artery disease continues to be one of the leading causes of morbidity and mortality, throughout the world. The typical etiology of coronary artery disease is characterized by the build-up of atherosclerotic plaque within the coronary arteries. Such deposits of atherosclerotic plaque tend to fully or partially block the flow of blood through the affected coronary arteries, and if untreated can result in myocardial ischemica, infarction and death.

For many years, the traditional surgical treatment of coronary artery disease has been coronary artery bypass surgery. In traditional coronary artery bypass surgery, the patient is generally anesthetized and placed on cardiopulmonary bypass. A thoracotomy is performed and the obstructed coronary blood vessels are exposed by surgical dissection. One or more segments of the patient's saphenous vein or internal mammary artery is/are harvested for use as bypass graft(s). The harvested segment(s) of vein or artery is/are then anastomosed to the obstructed coronary artery (ies) to form bypass conduit(s) around the arterial obstruction(s). Such traditional coronary artery bypass surgery is expensive, extremely invasive, and is associated with significant operative and perioperative complications.

One alternative to traditional coronary artery bypass surgery is balloon angioplasty. In balloon angioplasty, a flexible guide catheter is percutaneously inserted into a peripheral artery (e.g., the femoral artery) and is transluminally advanced through the vasculature until the distal tip of the catheter is within an obstructed coronary artery. Thereafter, a balloon catheter is passed through the guide catheter and into the obstructive lesion. The balloon of the balloon catheter is inflated one or more times to dilate coronary artery in the region of the obstructive lesion. These balloon angioplasty procedures tend to be less expensive and less traumatic than traditional coronary artery bypass surgery. However, balloon angioplasty procedures of this type have been associated with a significant incidence of restenosis at the angioplasty site. The cause and mechanism of such restenosis continues to be the subject of ongoing study. However, such restenosis has generally been attributed to either a) an increase in the mass of the artery wall (e.g., neointima formation), b) a thickening of the artery wall without substantial change in it's mass (e.g., vascular remodeling) and/or c) radial contraction of the balloon-dilated artery wall upon healing of cracks and fissures that have been created by the balloon dilation process.

Another alternative to traditional coronary artery bypass surgery is transluminal atheroectomy or ablation of the obstructive matter within the coronary artery. These transluminal atheroectomy or ablation procedures are performed by passing a catheter-mounted ablation apparatus through the vasculature to the site of the coronary obstruction. the catheter-mounted ablative apparatus is then utilized to cut, shave, sonicate, pulverize or otherwise ablate the obstructive matter from the lumen of the coronary artery. These atheroectomy or ablative procedures must be performed with caution to avoid abrasion or damage to the artery wall, as such abrasion or damage can result in excessive scaring and subsequent reocclusion of the artery lumen. Furthermore, these atheroectomy or ablative procedures may, in some cases at least, be confounded by the need to meticulously contain and remove the severed fragments of obstructive matter in order to prevent such fragments of obstructive matter from escaping into the patient's circulatory system. Examples of such atheroectomy catheters and other catheter-mounted ablative apparatus are described in U.S. Pat. No. 3,433,226 (Boyd), U.S. Pat. No. 3,823,717 (Pohlman, et al.), U.S. Pat. No. 4,808,153 (Parisi), U.S. Pat. No. 4,936,281 (Stasz), U.S. Pat. No. 3,565,062 (Kuris), U.S. Pat. No. 4,924,863 (Sterzer), 4B70,953 (Don Michael, et al.), U.S. Pat. No. 5,069,664 (Suess, et al.), U.S. Pat. No. 4,920,954 (Alliger, et al.) and U.S. Pat. No. 5,100,423 (Fearnot), as well as foreign patents/patent publications EP0347098A2 (Shiber), WO87-05739 (Cooper), WO89-06515 (Bernstein, et al.), WO90-0130 (Sonic Needle Corp.), EP316789 (Don Michael, et al.), DE 3,821,836 (Schubert), DE2438648 (Pohlman), and EP 0443256A1 (Baruch).

Other alternatives to traditional coronary artery bypass surgery have included minimally invasive endoscopic procedures which, ostensibly at least, can be performed through small (e.g., 1–3 cm) incisions formed in the patient's chest wall, by insertion of a thoracoscope and associated operative instruments through such incisions. One such thoracoscopic coronary bypass procedure is described in U.S. Pat. No. 5,452,733 (Sterman et al.). If perfected, these minimally invasive coronary artery bypass procedures may lessen the discomfort and length of recovery time experienced by patients who undergo such minimally invasive procedures vis a vis those who undergo traditional coronary artery bypass surgery. However, the performance of endoscopic surgical procedures of this type typically requires a great deal of operator skill and training. Furthermore, as with traditional coronary artery bypass surgery, the patients on whom these thoracoscopic procedures are performed are likely to undergo general anesthesia (with or without cardiopulmonary bypass) and the creation of a pneumothorax due to the formation of full-thickness incision(s) in the chest wall. Thus, many of the drawbacks associated with traditional coronary artery bypass surgery, are also associated with these minimally invasive thoracoscopic procedures.

Another previously described procedure for bypassing coronary artery obstructions utilizes a transmyocardial passageway (e.g., an interstitial tunnel formed in the muscular wall of the heart) to carry blood from the left ventricle of the heart to an obstructed coronary artery. Such procedure, hereinafter generally referred to as "Transmyocardial Direct Coronary Revascularization" (TMDCR) is described in U.S. Pat. No. 5,287,861 (Wilk), U.S. Pat. No. 5,409,019 (Wilk), and U.S. Pat. No. 5,429,114 (Wilk). The TMDCR methods described in these prior patents require that a catheter be introduced into the obstructed coronary artery and advanced through the obstructive lesion. After the catheter has been advanced through the obstructive lesion, the distal tip of the catheter is directed toward the artery wall and an opening (i.e., a transmycardial passageway) is formed through the artery wall, through the adjacent myocardium, and into the chamber of the left ventricle. Also, in this previously described TMDCR method, a stent is required to be positioned within the transmyocardial passageway. Such intramyocardial stent is constructed to perform a one-way valving function (i.e., to open and close the transmyocardial passageway in accordance with changes in the systolic-diastolic cardiac cycle). These TMDCR methods, previously described in U.S. Pat. No. U.S. Pat. No. 5,287,861 (Wilk), U.S. Pat. No. 5,409,019 (Wilk) and U.S. Pat. No. 5,429,114 (Wilk), may be difficult or impossible to perform in patients who suffer from total or near total obstructions of a coronary artery, because of the necessary for advancing the catheter through the coronary artery obstruction to accomplish creation of the transmyocardial passageway at a location which is downstream of the coronary obstruction. Furthermore, because these previously described TMDCR methods require placement of a stent within the transmyocardial passageway, such procedures are necessarily associated with procedural complexities associated with measuring and precutting the stent to a precise length so that it fits within the transmyocardial passageway without protruding into the chamber of the left ventricle and/or the lumen of the coronary artery. Also, any stent which is positioned solely within the transmyocardial passageway may be subject to repetitive flexing and/or stressing as the myocardium undergoes its normal contraction and relaxation. Such repeated flexing and/or stressing of the intramyocardial stent may lead to unwanted migration, dislodgement or damage of the stent.

In view of the above-summarized shortcomings and complexities of the previously described TMDCR methods, there exists a need in the art for the development of improved TMDCR methods and associated apparatus which may be utilized without the need for cumbersome stenting of the transmyocardial passageway and/or implantation of one-way valving apparatus within the transmyocardial passageway. Also, there exists a need for the development of a new TMDCR methods which can be performed in patients who suffer from total or near total coronary artery occlusions, without the need for advancing a catheter through such coronary artery occlusion(s).

SUMMARY OF THE INVENTION

The present invention provides new TMDCR methods, as well as certain valving devices which are usable in conjunction with these TMDCR methods.

i. TMDCR Procedures Using Coronary Vein

In accordance with the invention, there is provided a specific TMDCR method wherein a transmyocardial passageway is formed between a chamber of the heart (e.g., left ventricle) and a coronary vein. In this embodiment of the invention, blood may pass from the cardiac chamber, through the transmyocardial passageway, and into the coronary vein for the purpose of improving blood flow to the myocardium and/or to equalize or normalize pressures within the coronary venous vasculature by draining blood from the vein into the cardiac chamber. The coronary vein of this embodiment may be situated next to an obstructed coronary artery, and one or more secondary blood flow passageways may be created between the coronary vein and the adjacent artery, at site(s) which is/are downstream of the coronary artery obstruction. Also, the lumen(s) of the coronary vein and/or adjacent coronary artery may be blocked or embolized at appropriate positions to facilitate the flow of blood in the desired directions) through the man-made blood flow passageway(s), the coronary vein and/or the coronary artery. Additionally, one or more valving apparatus may be positioned within the coronary vein and/or within the cardiac chamber, to control or intermittently block the flow of blood through the transmyocardial passageway.

ii. TMDCR Procedures Using Unstented Transmyocardial Passageway

In accordance with the present invention, there is provided a method for coronary re-vascularization wherein an unstented transmyocardial passageway (e.g., a puncture tract, bore, tunnel, or other passageway) is formed between a chamber of the heart (e.g., the left ventricle) and a coronary vessel (e.g., a) an endogenous coronary artery; b) an endogenous coronary vein; c) a man-made passageway which has been formed in the heart, and which leads to an endogenous coronary vein; d) a man-made passageway which has been formed in the heart, and which leads to an endogenous coronary artery; and/or e) a man-made passageway which has been formed in the heart between an endogenous coronary artery and an endogenous coronary vein). The unstented transmyocardial passageway(s) created in accordance with this embodiment of the invention may be utilized to improve perfusion of the myocardium by shunting blood from the chamber of the heart (e.g., left ventricle) into the coronary vessel (e.g., vein artery or man-made passageway), or may alternatively be utilized to equalize or normalize flow or pressure within the cardiac vasculature by draining blood from one or more cardiac vessels (e.g., vein, artery or man-made passageway), into the chamber of the heart.

iii. Valving Devices Positionable in Coronary Vessels

Still further in accordance with the present invention, there are provided several types of intraluminal valving apparatus which may be positioned within the lumen(s) of the coronary blood vessel(s) (i.e., artery, vein or man-made passageway) which intersect with the transmyocardial passageway, to intermittently block bloodflow, in at least one direction, through the transmyocardial passageway. These intraluminal valving devices generally comprise tubular bodies having at least one occluder member positioned therein, said occluder member(s) being alternately moveable between i) open position(s) whereby bloodflow is permitted to pass through the transmyocardial bloodflow passageway in a desired direction, and ii) closed position(s) whereby blood is prevented from flowing through the transmyocardial bloodflow passageway, in an undesired direction.

iv. Tissue Valves For TMDCR Passageway

Alternatively, the present invention also includes endogenous tissue valve(s) which are formed in the transmyocardial passageway to perform a desired one-way valving function whereby blood is permitted to flow through the transmyocardial bloodflow passageway in a first direction, but is prevented from backflowing or regurgitating in a second direction.

v. Intracardiac Valving Devices For TMDCR Passageway

Still further in accordance with the present invention, there are provided intracardiac valving devices which are mountable within a chamber of the heart (e.g., left ventricle) immediately adjacent to an opening into a transmyocardial passageway which extends from the cardiac chamber to a coronary vessel (e.g., artery, vein or man-made passageway). Such intracardiac valving device may be constructed such that it will open in response to hemodynamic pressure generated during systole and/or in response to mechanical contraction (i.e., shortening and thickening) of the myocardium during systole. When open, the intracardiac valving device permits blood to flow through the transmyocardial bloodflow passageway. Thereafter, the valving device may be constructed to close when diastolic pressures are present in the cardiac chamber or when the myocardium undergoes mechanical relaxation (i.e., lengthening and thinning during diastole. When closed, the valving device will prevent blood from backflowing or regurgitating from the transmyocardial bloodflow passageway, into the cardiac chamber.

iv. Protrusive Stents and Stented Grafts For TMDCR Passageways

Still further in accordance with the present invention, there are provided stents and stented grafts which are positionable within the transmyocardial passageway, and which protrude into the adjacent coronary vessel (e.g., vein, artery or man-made passageway). These protrusive stents and/or protrusive stented grafts may be self-expanding or pressure-expandable. Optionally, one or more valves or occluder members may be positioned within such protrusive stents and/or stented grafts to facilitate valving or directed movement of bloodflow in accordance with the diastolic/systolic cardiac cycle.

Further objects and advantages of the present invention will become apparent to those skilled in the art upon reading and understanding of the following detailed descriptions of preferred embodiments.

BRIEF DESCRIPTION OF THE DRAWINGS

FIG. 8b is a longitudinal sectional view showing an alternative embodiment of the protrusive stent apparatus shown in FIG. 5a.

DETAILED DESCRIPTION OF THE PREFERRED EMBODIMENTS

The following detailed description and the accompanying drawings are provided for purposes of describing and illustrating presently preferred embodiments of the invention only, and are not intended to limit the scope of the invention in any way.

Upon making reference to the accompanying figures, it will be noted that many of the figures include showings of human cardiovascular anatomy. The various anatomical structures shown in the figures are labeled in accordance with the following legend:

| | |
|---|---|
| AO | Aorta |
| CBV | Coronary Blood Vessel (artery, vein or man-made passageway) |
| CA | Coronary Artery |
| CAL | Coronary Artery Lumen |
| CV | Coronary Vein |
| CVL | Coronary Vein Lumen |
| IVC | Inferior Vena Cava |
| SVC | Superior Vena Cava |
| LV | Left Ventricle |
| RV | Right Ventricle |
| IVS | Intraventricular Septum |
| M | Myocardium | i. TMDCR Method Utilizing Coronary Vein

With reference to FIGS. 1–4, the present invention includes methods for improving perfusion of regions of the myocardium M which are ischemic or otherwise affected by the existence of an obstruction OB within a coronary artery CA, by forming a transmyocardial passageway 10 which extends from a chamber of the heart, (e.g., left ventricle LV), to a coronary vein Cv.

Figure 1:
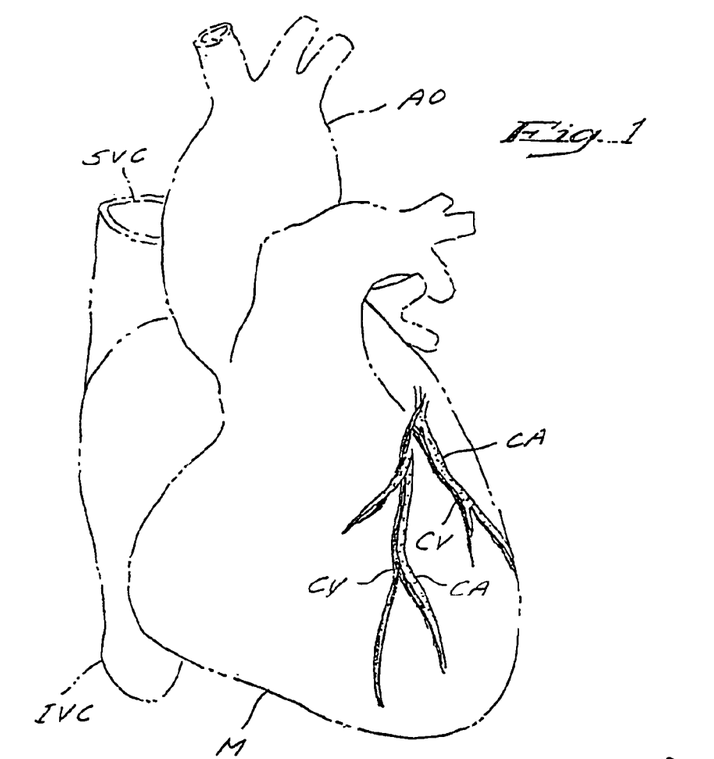
FIG. 1 is a perspective view of a human heart showing the typical anatomical positioning of the coronary arteries and coronary veins of the left heart.
Figure 1A:
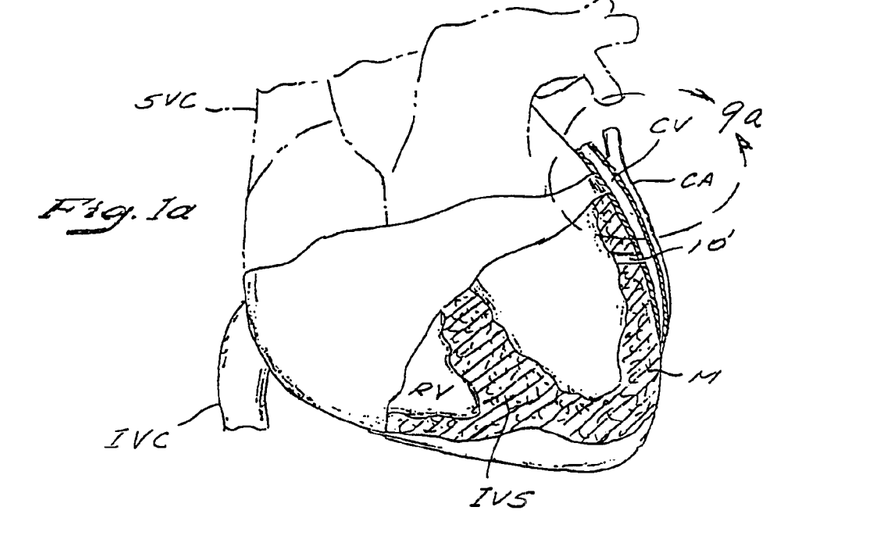
FIG. 1a is a partial cut-away sectional view of a human heart wherein a transmyocardial passageway has been created between the left ventricle and a coronary vein, in accordance with the present invention.
Figure 1B:
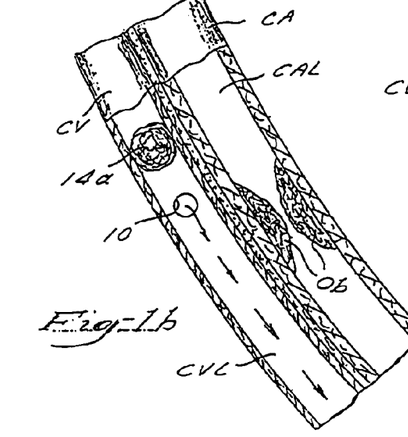
FIG. 1b is a partial longitudinal sectional view through an obstructed coronary artery and adjacent coronary vein, showing a transmyocardial passageway of the present invention, extending between the chamber of the left ventricle and the coronary vein.

In some embodiments of this method, the transmyocardial passageway 10 will simply provide a flow of blood from the chamber of the heart and into the coronary vein CV, such that the blood will pass in retrograde fashion through the coronary vein CV to perfuse the ischemic portion of the myocardium through the coronary vein, as sheen in FIG. 1b.

Figure 1C:
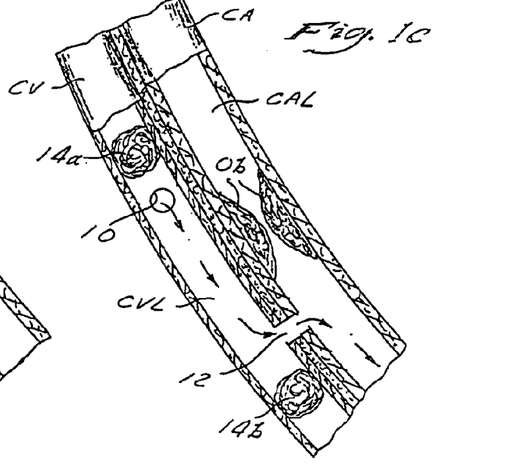
FIG. 1c is a partial longitudinal sectional view through an obstructed coronary artery and adjacent coronary vein, showing a transmyocardial passageway of the present invention extending between the chamber of the left ventricle to the coronary vein, and a secondary bloodflow passageway extending from the coronary vein to the adjacent coronary artery, downstream of the obstruction.
Figures 1D, 2, 2A, 2B, 3:
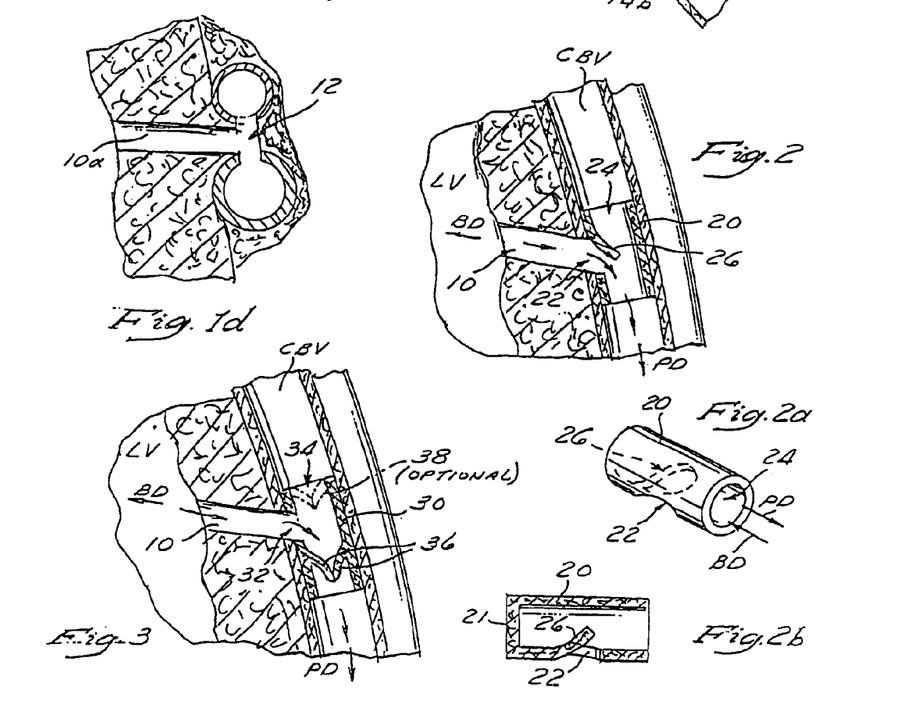
FIG. 1d is a partial longitudinal sectional view through a portion of the myocardium of a human heart, adjacent the left ventricle, showing an alternative embodiment of the present invention wherein a transmyocardial bloodflow passageway extends from the chamber of the left ventricle to a secondary passageway which has been created between the obstructed coronary artery and the adjacent coronary vein.
FIG. 2 is a longitudinal sectional view showing a first embodiment of an intravascular valving apparatus of the present invention operatively positioned within a coronary blood vessel (artery, vein or man-made passageway).
FIG. 2a is a perspective view of the intravascular valving apparatus of FIG. 2.
FIG. 2b is an elevational view of a variant of the intravascular valving apparatus shown in FIGS. 2 and 2a, wherein a bloodflow blocking bulkhead is formed on the upstream end of the apparatus.
FIG. 3 is a longitudinal sectional view of a second embodiment of an intravascular valving apparatus of the present invention operatively positioned in a coronary blood vessel (artery, vein or man-made passageway).

In other embodiments of the invention, a secondary bloodflow passageway 12 may be created between the coronary vein CV into which the transmyocardial passageway 10 extends and the obstructed coronary artery CA, at a location which is downstream of the obstruction OB, as shown in FIG. 1c. The formation of this secondary bloodflow passageway 12 allows blood from the chamber of the heart (e.g., the left ventricle LV) to initially flow through the transmyocardial passageway 10, through a segment of the coronary vein lumen CVL, through the secondary bloodflow passageway 12, and into the coronary artery lumen CAL, at a location downstream of the coronary artery obstruction OB, as shown in FIG. 2b. The secondary bloodflow passageway 12 which extends between the coronary vein CV and the coronary artery CA may optionally be stented or internally supported by a stent, sleeve or coating (e.g., a polymer coating) to maintain patency of the secondary passageway 12.

In at least some applications, the coronary vein lumen CVL may be purposely blocked (e.g., ligated, embolized, fused, welded, clamped, etc.) at site(s) upstream and/or downstream of the transmyocardial passageway 10. As shown in FIG. 1b, when the transmyocardial passageway 10 formed for the purpose of shunting oxygenated blood into the coronary vein lumen CVL, a proximal embolization member 14a may be positioned within the coronary vein lumen CVL, immediately upstream of transmyocardial passageway 10, to ensure that the shunted blood will flow, in the desired retrograde direction through the coronary vein CV. Similarly, as shown in FIG. 1c, when a secondary bloodflow passageway 12 is formed to carry the oxygenated blood from the coronary vein lumen CVL into the coronary artery lumen CAL, downstream of the obstruction OB, a distal embolization member 14b may be positioned within the coronary vein lumen CVL immediately downstream of the secondary bloodflow passageway 12, to divert the flow of blood through the secondary bloodflow passageway 12.

Examples of methods for forming the optional secondary bloodflow passageway(s) 12 between the coronary vein CV and coronary artery CA are described in United States Provisional Specification No. 60/005,164, filed Oct. 13, 1995 and 60/010,614 filed Feb. 2, 1996, the entire disclosures of which are expressly incorporated herein by reference.

The proximal embolization member 14a and/or distal 14b embolization member may comprise any suitable type of lumen blocking matter or apparatus, examples of which are the embolization coils described in U.S. Pat. No. 5,382,260 (Dormandy, Jr. et al.), U.S. Pat. No. 5,108,407 (Geremia et al.), and U.S. Pat. No. 5,256,146 (Ensminger, et al.). Alternatively, the coronary vein lumen CVL may be closed off at the sites of the proximal 14a and/or distal 14b embolization members by any suitable alternative means, such as clamping, clipping, ligating, fusing, welding or adhesively conjoining the inner walls of the coronary vein lumen CVL so as to provide the desired blocking of bloodflow therethrough.

FIG. 1d shows an alternative embodiment of the method of the present invention wherein a secondary bloodflow passageway 12 of the above-described type has been created between the coronary vein CV and coronary artery CA, and wherein the transmyocardial bloodflow passageway 10a extends from the chamber of the heart (e.g., left ventricle) such secondary bloodflow passageway 12.

ii. TMDCR Methods Employing Non-Stented Transmyocardial Passageway

The present invention also includes alternative TMDCR methods wherein a transmyocardial passageway 10 is formed between a chamber of the heart and a coronary vessel (i.e., a) an endogenous coronary vein, b) an endogenous coronary artery, c) a man-made passageway in the heart which connects to an endogenous coronary vein; d) a man-made passageway in the heart which connects to an endogenous coronary or e) a man-made passageway which extends between an endogenous coronary artery and an endogenous coronary vein), and such transmyocardial passageway 10 is allowed to remain non-stented (e.g., devoid of any stent or internal support member positioned therewith).

The utilization of a non-stented transmyocardial passageway 10 in accordance with this embodiment of the present invention eliminates the need for precise measurement, precutting to length and insertion of a stent apparatus within the transmyocardial passageway 10, as is required of the previous TMDCR method described in U.S. Pat. No. 5,287,861 (Wilk), U.S. Pat. No. 5,409,019 (Wilk) and U.S. Pat. No. 5,429,114 (Wilk). When the non-stented transmyocardial passageway 10 of the present invention is intended to provide bloodflow from the chamber of the heart (e.g., left ventricle) into the coronary vessel (e.g., vein, artery or man-made passageway), the non-stented transmyocardial passageway 10 must remain open during systolic contraction of the myocardium. If the non-stented passageway 10 is permitted to substantially occlude or close-off during systolic contraction of the myocardium, such could prevent or deter the desired blood flow from passing through the transmyocardial passageway 10. In this regard, in embodiments of the invention which utilize the non-stented transmyocardial passageway 10, it may be desirable to debulk, core or otherwise enlarge the diameter of the passageway 10 during it's formation so as ensure that the passageway 10 will remain patent and open, even during systolic contraction of the myocardium. Such coring, debulking or other enlargement of the passageway 10 may be accomplished by any suitable means, including the use of a hollow coring needle, laser, electrosurgical probe, or other tissue removing/ablating device capable of debulking and removing tissue so as to create a transmyocardial passageway 10 of the desired diameter.

Also, it will be appreciated that the non-stented transmyocardial passageway preferably should not fill-in with granulation tissue or otherwise close-off as a result of any scarring or healing process of the myocardium. In this regard, the coring, de-bulking or other enlargement of the non-stented passageway 10 and/or the continuing passage of blood, therethrough, may be sufficient to prevent or deter such scarring or natural closing of the non-stented passageway 10. However, in applications wherein scarring or natural closing of the non-stented passageway 10 is a potential problem, it may be desirable to cauterize, heat, chemically treat or coat the walls of the non-stented passageway to prevent or deter blocking of such passageway by scarring or in growth of the myocardial tissue.

iii. Valving Apparatus Positionable in the Coronary Vessel(s) to Prevent Backflow Into the Transmyocardial Bloodflow Passageway In many embodiments of the invention, the transmyocardial passageway 10, 10a may function in it's intended manner without the inclusion of any valving apparatus, for intermittently blocking the flow of blood therethrough. However, in at least some applications, it may be desired to prevent the backflow of blood through the transmyocardial passageway 10, 10a during certain phase(s) of the cardiac cycle when the relative hemodynamic pressures would tend to cause such backflow. In this regard, the present invention includes intravascular valving apparatus 20, 30, 31, 33, 40, examples of which are shown in FIGS. 2–4. These intravascular valving apparatus 20, 20, 31, 33, 40 are positionable within the lumen of the coronary blood vessel CBV (e.g., vein, artery or man-made passageway), and operate to prevent backflow of blood into the transmyocardial bloodflow passageway 10, 10a.

In general, each of the intravascular valving apparatus 20, 30, 31, 33, 40 of the present invention comprise a radially expandable cylindrical or tubular body which is transluminally advanceable into the lumen of the coronary blood vessel CBV (e.g., artery, vein or man-made passageway), and which is then radially expandable so as to become implanted at a location which is adjacent or near to the intersection of that coronary vessel CBV with a transmyocardial bloodflow passageway 10, 10a. The valving apparatus 20, 30, 31, 33, 40 has an axial bore 24, 34, 42 through which blood may pass as it flows through the lumen of the coronary blood vessel CBV or secondary passageway 12 in which the apparatus 20, 30, 31, 33, 40 is positioned. One or more occluder members 26, 36, 46 are formed within the apparatus 20, 30, 31, 33, 40. Such occluder member(s) 26, 36, 46 are alternately moveable between a first (e.g., open) position whereby blood is permitted to flow from the transmyocardial bloodflow passageway into the coronary blood vessel CBV or secondary passageway 12, and a second (e.g., closed) position whereby blood is prevented or deterred from backflowing or regurgitating from the coronary blood vessel CBV or secondary passageway 12, into the transmyocardial bloodflow passageway.

Individual embodiments of the intravascular valving apparatus 20, 30, 31, 33, 40 are described in more detail herebelow. It will be appreciated, however, that each of the intravascular valving apparatus 20, 30, 31, 33, 40 of the present invention offer advantages over the intramyocardial stenting/valving apparatus described in U.S. Pat. No. 5,248,861 (Wilk), U.S. Pat. No. 5,409,019 (Wilk) and U.S. Pat. No. 5,429,144 (Wilk) in that they are operatively situated entirely within the lumen of the coronary blood vessel CBV of secondary passageway 12 and do not extend into the transmyocardial passage way (e.g., the first passageway 10, 10a) which emanates from the chamber (e.g., left ventricle) of the heart. In this regard, the valving apparatus 20, 30, 31, 33, 40 of the present invention do not require precise measurement or precise cutting-to-length, as is purportedly required of the intramyocardial stenting/valving apparatus described in U.S. Pat. No. 5,248,861 (Wilk), U.S. Pat. No. 5,409,019 (Wilk) and U.S. Pat. No. 5,429,144 (Wilk).

It is desirable that the valving apparatus 20, 30, 31, 33, 40 of the present invention be initially disposable in a first radially compact diameter which is small enough to be mounted upon or inserted into an intravascular delivery catheter. Such intravascular delivery catheter, having the valving apparatus 20, 30, 31, 33, 40 mounted thereon or therewithin, is transluminally passable through the vasculature and into the lumen of the coronary blood vessel CBV wherein the apparatus 20, 30, 31, 33, 40 is to be implanted. Thereafter, the apparatus 20, 30, 31, 33, 40 is radially expanded (by self-expansion or pressure-expansion) to a second radially expanded diameter, wherein the outer surface of the apparatus 20, 30, 31, 33, 40 frictionally engages the surrounding wall of the coronary blood vessel CBV such that the apparatus 20, 30, 31, 33, 40 is thereby implanted and retained in a stationary position. When the valving apparatus 20, 30, 31, 33, 40 is so implanted within the coronary blood vessel CBV, blood may flow through the axial bore 24, 34, 42 of the apparatus 20, 30, 31, 33, 40, as described in more detail herebelow.

It is to be appreciated that the valving apparatus 20, 30, 31, 33, 40 may be either self-expanding or pressure expandable. In this regard, if the valving apparatus 20, 30, 31, 33, 40 is "self-expanding", the cylindrical body of the apparatus 20, 30, 31, 33, 40 may be formed of a shape memory alloy or resilient material (e.g., spring metal) which is inherently biased to it's second radially expanded diameter. Alternately, in embodiments wherein the valving apparatus 20, 30, 31, 33, 40 is, "pressure-expandable", the cylindrical body of the apparatus 20, 30, 31, 33, 40 may be formed of plastically deformable material which is initially formed it's first radially compact diameter, and which may be pressure deformed to it's second radially expanded diameter by the exertion of outward force from an internally positioned balloon or other radial expansion device.

It is to be further appreciated that the potential useability and applicability of the intravascular valving apparatus 20, 30, 31, 33, 40, 50 described herebelow is not limited only to uses in connection with the improved TMDCR methods of the present invention, but may also be useable as a modification of the previously described TMDCR methods, such as those of U.S. Pat. No. 5,287,816(Wilk), U.S. Pat. No. 5,409,019(Wilk), and U.S. Pat. No. 5,429,144 (Wilk).

a. Intravascular Valving Apparatus

First Embodiment

FIGS. 2, 2a and 2b show a first embodiment of an intravascular valving apparatus 20 which is positioned within the lumen of a coronary blood vessel CBV (artery, vein or man-made passageway), at a location which is adjacent it's intersection with the transmyocardial passageway 10. This embodiment of the valving apparatus 20 has a cylindrical body having an axial bore 24 which extends longitudinally therethrough, and a side aperture 22 formed in the sidewall thereof. The side aperture 22 is preferably the same size or larger than the diameter of the adjacent end of the transmyocardial passageway 10, such that blood flowing from the cardiac chamber (e.g., left ventricle LV) through the transmyocardial passageway 10 will pass directly through the side aperture 22 and into the bore 24 of the valving apparatus 20. An occluder member 26, such as a hinged obturator or pliable elastomeric leaflet is affixed to the cylindrical body of the valving apparatus 20, and extends over and substantially blocks the side aperture 22 so as to prevent the flow of blood out of the side aperture 22. The occluder member 26 is alternately moveable between a first position wherein it blocks blood from flowing out of the side aperture 22, and a second position wherein it permits blood to flow into the bore 24 through the side aperture 22.

This first embodiment of the valving apparatus 20 may be implanted in the lumen of the coronary blood vessel CBV such that the side aperture 22 is in alignment with the adjacent end of the bloodflow passageway 10. During systolic contraction of the heart the relatively high pressure within the left ventricle will force the occluder member 26 to its second (open) position, allowing blood to flow from the left ventricle, through the transmyocardial passageway 10, through the side aperture 22, through the bore 24 and into the lumen of the coronary blood vessel CBV in the perfusive direction PD, as shown. Thereafter, during systolic relaxation of the heart, the relatively low filling pressure within the left ventricle LV will draw the occluder member 26 to its first (closed) position whereby the occluder member 26 will prevent blood from regurgitating or moving in the backflow direction BD from the lumen of the coronary blood vessel CBV, out of the side aperture 22, and into the bloodflow passageway 10. In this manner the first embodiment of the valving apparatus serves to facilitate efficient pumping of oxygenated blood from the left ventricle and into the lumen of the coronary blood vessel CBV, to improve the flow of oxygenated blood to an ischemic or blood-flow-deprived region of the myocardium M.

As shown in FIG. 2a, a closure member 21, in the nature of an end cap, may be formed on the upstream end of the apparatus 20 so as to completely or substantially block the flow of blood through the coronary blood vessel CBV and into the upstream end of the bore 24 of the apparatus 20. The optional inclusion of the end closure member 21 in the apparatus 20 may serve to obviate any need for the placement of a proximal embolization member 14a within the lumen of the coronary blood vessel CBV, upstream of the valving apparatus 20.

b. Intravascular Valving Apparatus

Second Embodiment

FIG. 3 shows a second embodiment of the intravascular valving apparatus 30 which comprises a generally cylindrical body having an axial bore 34 extending longitudinally therethrough and a pair of occluder members 46 positioned therewithin, and a side aperture 32: formed in the cylindrical sidewall of the apparatus 30, behind the occluder members 36. Each occluder member 36 is affixed at least one point to the cylindrical body of the apparatus 30, and may comprise any suitable structure or openable and closeable passage, such as a self-sealing slit or hole, or a hinged leaflet or pliable elastomeric member. The occluder members 46 are alternately moveable between first positions wherein the occluder members 36 directly contact one another so as to prevent blood from backflowing in the backflow direction BD through the axial bore 34 of the apparatus 30, and second positions wherein the occluder members 36 move out of contact with one another such that blood may flow through the axial bore 34 of the apparatus 30 in the perfusion direction PD. The side aperture 32 is preferably as large as or larger than the diameter of the bloodflow passageway 10 which extends through the myocardium M from the left ventricle LV to the lumen of the coronary blood vessel CBV. This embodiment of the apparatus 30 is implanted in the lumen of the coronary blood vessel CBV such that its side aperture 32 is directly aligned with the bloodflow passageway 10 so that blood may flow through the bloodflow passageway 10, into the axial bore 34 of the apparatus 30.

During systolic contraction of the heart the relatively high pressures created in the left ventricle LV will force blood to flow through the passageway 10 into the axial bore 34 of the valving apparatus 30. Such systolic bloodflow will move the occluder members 36 to their second (i.e., open) positions, thereby allowing the blood to flow through the lumen of the coronary blood vessel in the perfusion direction PD. Thereafter, when the heart undergoes diastolic relaxation, the relatively low filling pressures created within the left ventricle LV will draw the occluder members 36 to their first (ie. closed) positions, thereby preventing blood from regurgitating or backflowing out of the side aperture 32, in the backflow direction BD. In this manner, this second embodiment of the intravascular valving apparatus 30 serves to facilitate efficient pumping of oxygenated blood from the left ventricle LV and through the lumen of the coronary blood vessel CBV, in order to provide improved bloodflow to an ischemic or blood-flow-deprived region of the myocardium M.

Optionally, secondary occluder members 38 may be formed or mounted within the bore 34 of the apparatus 30, upstream of the side opening 32. These optional secondary occluder members 38 may be of the same type and construction as the above-described downstream occluder members 36. If present, such additional occluder members 38 will assume their first (e.g., closed) position when the pressure of blood within the bore 34 of the apparatus 30 downstream of such secondary occluder members 38 is greater than the pressure of blood within the coronary blood vessel CBV upstream of the such secondary occluder member 38. In this regard, the provision of such secondary occluder members 38 within the apparatus 30 will obviate the need for placement of a proximal occlusion apparatus 14a within the lumen of the coronary blood vessel CBV upstream of the transmyocardial bloodflow passageway 10. The inclusion of such secondary occluder members 38, or the alternative use of a proximal occlusion member 14a, will be of particular importance when the coronary blood vessel CBV is a coronary vein CV, due to the substantial difference between endogenous coronary venous blood pressures and those pressures which will be created by systolic arterial bloodflow through the coronary vein, downstream of the transmyocardial bloodflow passageway 10.

Figure 3A:
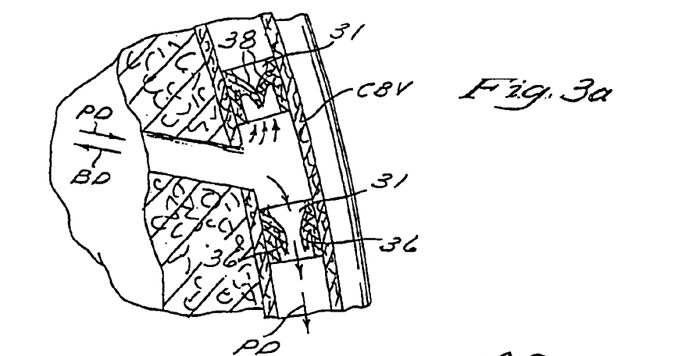
FIG. 3a is longitudinal sectional view showing variant of the second intravascular valving apparatus embodiment shown in FIG. 3, wherein two (2) separate valving apparatus are respectively positioned upstream and downstream of the junction between the transmyocardial bloodflow passageway and the coronary blood vessel (artery, vein or man-made passageway).
Figure 4:
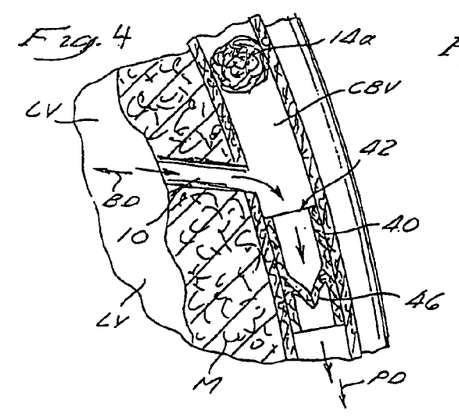
FIG. 4 is a longitudinal sectional view showing a third embodiment of an intravascular valving apparatus of the present invention operatively positioned within a coronary blood vessel (artery, vein or man-made passageway).

FIG. 3a shows one variant of the second embodiment wherein two (2) separate intravascular valving apparatus 31a, 31b are respectively positioned upstream and downstream of the transmyocardial bloodflow passageway. The above-described occluder members 36 are formed in the apparatus 31b which is positioned downstream of the transmyocardial bloodflow passageway 10 and the above described secondary occluder members 38 are formed within the apparatus 31a which is positioned upstream of the transmyocardial bloodflow passageway 10. In this manner, these separate intravascular valving apparatus 31a, 31b, will function in the same manner as the apparatus 30 shown in FIG. 3, when it is equipped with the optional secondary occluder members 38. However, it will be appreciated that these separate intravascular valving apparatus 31a, 31b do not have any side aperture 32, as does the device shown in FIG. 3, and accordingly, will obviate any need for correctly sizing an aligning such side aperture 32 with the transmyocardial bloodflow passageway 10.

Figure 3B:
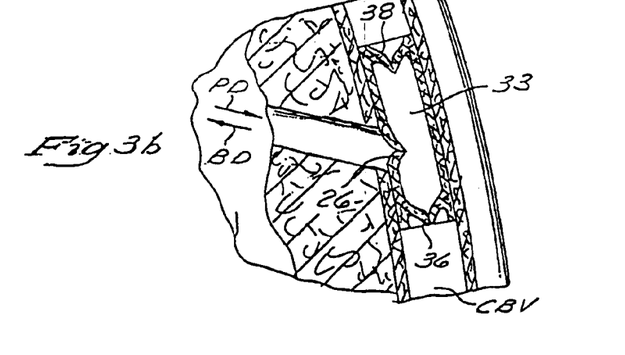
FIG. 3b is a longitudinal sectional view of another variant of the second intravascular valving apparatus embodiment shown in FIG. 3, wherein three (3) valves are incorporated within a single tubular body to accomplish valving of bloodflow through a transmyocardial bloodflow passageway and coronary blood vessel (artery, vein or man-made passageway).

FIG. 3b shows another variant of the second embodiment wherein a single intravascular valving apparatus 33, in the nature of a tubular stent or tubular body, is provided with three (3) separate valves 26, 36, 38 at locations which are a) at the junction of the transmyocardial passageway 10 and the coronary blood vessel CBV, b) upstream of the transmyocardial passageway 10 and c) downstream of the transmyocardial passageway 10, respectively. These valves 26, 36, 38 may comprise self-sealing pliable slit openings, elastomeric leaflets, hinged occluder members or any other suitable type of structure or apparatus which will intermittently open and clone, to permit bloodflow in the desired direction therethrough. For example, in applications wherein it is desired for the transmyocardial passageway 10 to provide a flow of blood from the cardiac chamber into the coronary blood vessel CBV, the first valve 26 will operate to open during systole to permit blood to flow from the transmyocardial passageway 10 into the coronary blood vessel CBV, but will close during diastole to prevent backflow or regurgitation into the cardiac chamber. Similarly, the second (upstream valve 38 will close during systole to prevent backflow of blood through the proximal end opening of the valving apparatus 33. The third (downstream) valve 36 will open during systole to permit the desired flow of blood entering through the transmyocardial passageway 10, to continue on downstream through the coronary blood vessel CBV in the desired perfusion direction.

c. Intravascular Valving Apparatus

Third Embodiment

FIG. 4 shows a third embodiment of the intravascular valving apparatus 40 which comprises a generally cylindrical body having an axial bore 42 extending longitudinally therethrough and a plurality of occluder members 46 formed therewithin. The cylindrical body and occluder members 46 of this third embodiment of the apparatus 40 are the same as those of the above described second embodiment, except that the cylindrical body of this third embodiment is devoid of any side aperture(s) or openings in the cylindrical sidewall. In contrast to the above described second embodiment 30, this third embodiment of the apparatus 40 is implanted in the lumen of the coronary blood vessel CBV at a location which is downstream of the junction between the coronary blood vessel CBV and the first bloodflow passageway 10.

Figure 5:
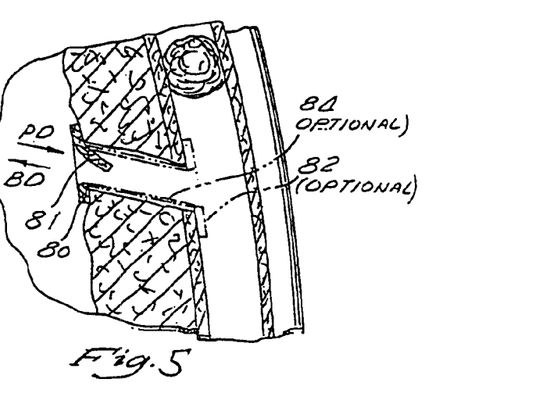
FIG. 5 is a longitudinal sectional view showing an intracardiac valving apparatus of the present invention along with an optional retainer assembly (dotted lines) useable to mount such intracardiac valving apparatus on the inner wall of the heart.
Figure 5A:
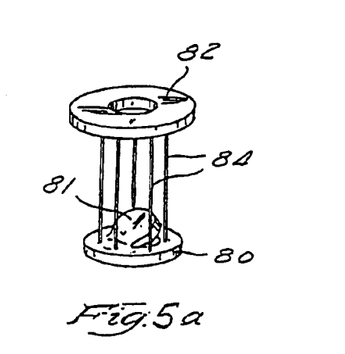
FIG. 5a is a perspective view of the intracardiac valving apparatus of FIG. 4 having the optional retainer assembly affixed thereto.

It will be appreciated that the individual features and attributes of each of the above-described embodiments of valving apparatus 20, 30, 31, 33, 40 may be incorporated into any or all of the other above-described valving apparatus 20, 30, 31, 33, 40 as feasible, to accomplish the desired hemodynamic bloodflow within the coronary vasculature.

iv. Intracardiac Valving Apparatus For Controlling Bloodflow Through the Transmyocardial Passageway FIGS. 5 and 5a show examples of intracardiac valving apparatus 80 which may be utilized to prevent backflow of blood through the transmyocardial passageway 10, or to otherwise control the flow of blood through the transmyocardial passageway 10 in accordance with the systolic/diastolic cardiac cycle.

As shown, the intracardiac valving apparatus, 80 is positionable within the cardiac chamber (e.g., left ventricle) immediately adjacent the opening of the transmyocardial passageway 10 thereinto. The intracardiac valving apparatus 80 may comprise any suitable type of hinged, pliable or moveable occlusion member or self-sealing slit which will operate to intermittently block or unblock the flow of blood in at least one direction through the transmyocardial passageway 10. In the embodiment shown in FIGS. 5, 5a, the intracardiac valving apparatus 80 comprises a generally annular body having a central aperture formed therein and an occluder member 81, such as a pliable elastomeric flap, mounted within the aperture. The occluder member 81 will move, in relation to hemodynamic bloodflow and/or contraction of the myocardium M, between an open position whereby blood is permitted to pass in at least one direction through the transmyocardial passageway 10, and a closed position whereby blood is prevented from flowing in at least one direction through the transmyocardial passageway 10.

The intracardiac valving apparatus 80 may be implanted within the cardiac chamber by any suitable surgical or non-surgical technique. Preferably, the intracardiac Valving apparatus 80 is initially positioned within or upon a delivery catheter, and the delivery catheter is advanced through the coronary blood vessel CBV, and through the transmyocardial passageway 10. Thereafter, the intracardiac valving apparatus 80 is released or ejected from the delivery catheter, and is caused to radially expand to it's operative configuration. the expanded valving apparatus 80 is then retracted into abutting contact with the myocardial wall, as shown.

The intracardiac valving apparatus 80 may be attached to the myocardial wall by any suitable attachment such as hooks, sutures, adhesives or a retaining assembly which is operative to hold the intracardiac valving apparatus 80 in its desired fixed position upon the myocardial wall. One such retaining apparatus, shown in FIGS. 5 and 5a, comprises an annular retaining ring 82 which is positionable within the coronary blood vessel CBV and a plurality of elastomeric tether members 84 which extend between the retainer ring 82 and the intracardiac valving apparatus 80. In this manner, the elastomeric tethers 84 will resiliently draw the retaining ring 82 and intracardiac valving apparatus 80 toward one another, so as to hold the intracardiac valving apparatus 80 in fixed abutment with the myocardium M as shown.

In some embodiments of the intracardiac valving apparatus 80, the occluder member 81 will be designed to move in response to changes in hemodynamic pressure, such that when the hemodynamic pressure within the cardiac chamber (e.g., left ventricle) exceeds that within the transmyocardial passageway 10, the occluder member 81 will move to it's open position, and when the pressure within the transmyocardial passageway 10 exceeds that within the cardiac chamber (e.g., left ventricle) the occluder member 81 will move to it's closed position.

Alternatively, in other embodiments of the intracardiac valving apparatus 80, the occluder member 81 may be designed to move in relation to contractile changes in the myocardial muscle. In these embodiments, the occluder member 81 will be mechanically linked or coupled to the body of the intracardiac valving apparatus 80 such that, when the myocardium undergoes contraction (e.g., shortening and thickening), the occluder member 81 will be propelled to it's open position, and when the myocardium undergoes relaxation (e.g., lengthening and narrowing) the occluder member 81 will move to it's closed position.

In this manner, the intracardiac valving apparatus 80 of the present invention serves to control the desired bloodflow through the transmyocardial passageway 10, without the need for customizing or precise cutting-to-size of any intramyocardial stent, as has been described in the prior art.

v. Tissue Valve for Preventing Backflow into the Transmyocardial Bloodflow Passageway.

An alternative to the use of the above-described intravascular valving apparatus 20, 30, 31, 33, 40 and/or the intracardiac valving apparatus 80, is an endogenous tissue valve which may be formed within the transmyocardial passageway 10 or at either end thereof. For example, FIGS. 6a–6b show an endogenous tissue valve 50 which is formed at the junction of the transmyocardial bloodflow passageway 10 and a coronary blood vessel CBV (e.g., artery vein or man-made passageway).

Figure 6A:
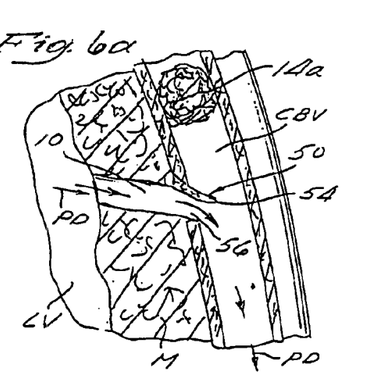
FIGS. 6a and 6b are longitudinal sectional views of a human heart wherein a bloodflow passageway has been created between the left ventricle and a coronary blood vessel (artery, vein or man-made passageway), and a valving tissue valve has been created in the wall of the blood vessel, in accordance with the present invention.
Figure 6B:
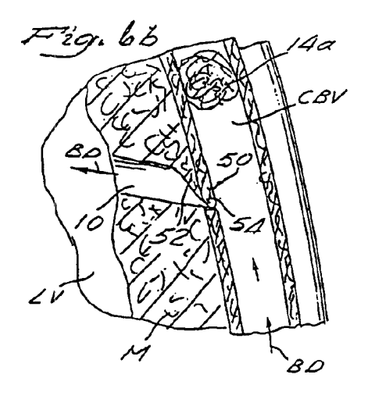

With reference to FIGS. 6a–6b, the endogenous tissue valve 50 may comprise one or more segment(s) 54 of the wall of the coronary blood vessel CBV, along with one or more tapered segment(s) of underlying myocardial tissue 52.

This endogenous tissue valve 50 is formed such that the segment(s) of blood vessel wall 54 and underlying portion(s) of myocardial tissue 52 will receive sufficient blood supply so as not to become necrotic or infarcted. The thickness and mass of the tissue valve 50 is preferably defined so that, when the heart undergoes systolic contraction the elevated pressure created within the left ventricle LV and transmyocardial bloodflow passageway 10 will force the tissue valve 50 to an open position, as illustrated in FIG. 5a, thereby creating an opening 56 through which blood may flow into the lumen of the coronary blood vessel CBV, in the profusion direction PD. Thereafter, when the heart undergoes diastolic relaxation the relatively low filling pressures within the left ventricle LV and transmyocardial bloodflow passageway 10 will allow the tissue valve 50 to return to a second or closed position, as illustrated in FIG. 5b. When in such second or closed position, the tissue valve 50 will substantially or completely close off the transmyocardial bloodflow passageway 10, so as to prevent blood from backflowing or regurgitating in the backflow direction BD, from the lumen of the coronary blood vessel CBV into the transmyocardial bloodflow passageway 10.

The tissue valve 50 may be created by any suitable means, including a procedure whereby the tissue penetrating, cutting or boring device used to create the transmyocardial bloodflow passageway is provided with a tapered distal end having a configuration analogous to that of the inner edge(s) 55 of the wall segment(s) 54 so as to form the desired tissue valve(s) or segment(s) when form the endogenous tissue valve 50, or by another catheter-based device which is equipped to form such tissue valve(s) or segment(s).

It will be appreciated that the tissue valve 50 may be formed in various configuration. For example, although the tissue valve 50 shown in FIGS. 6a and 6b hereof consists of a single flap, various alternative configurations may be utilized wherein multiple tissue protrusions, multiple tissue flaps, or annularly tapered or funnel shapped tissue flaps are formed to perform the desired valving function. Any and all such configurations of endogenous tissue are intended to be included within the scope of the term "tissue valve" 50 as used herein.

vi. Elastic Closure for Preventing Backflow Into the Transmyocardial Bloodflow Passageway.

Figure 7A:
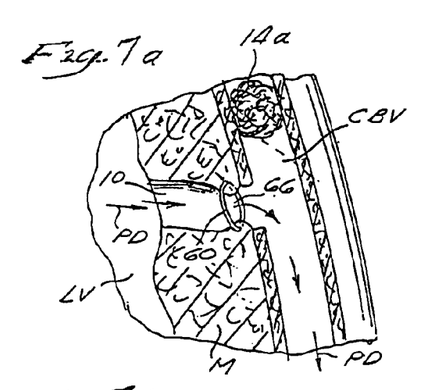
FIGS. 7a–7b are longitudinal sectional views of a human heart wherein a blood vessel passageway has been created between the left ventricle and a coronary blood vessel (artery, vein or man-made passageway), and wherein an elastic suture has been positioned, in accordance with the present invention.
Figure 7B:
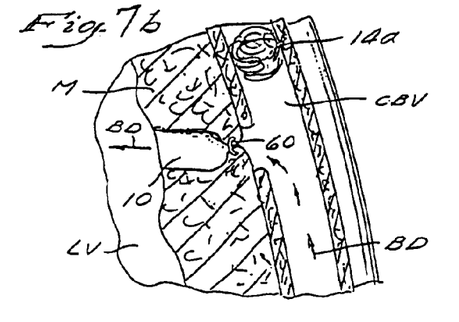

An alternative to the mechanical valving apparatus 20, 30, 31, 33, 40 or endogenous tissue valve 50 is the elastic closure member 60, shown in FIGS. 7a and 7b.

The elastic closure member 6d may comprise one or more sutures formed of stretchable or elastic material such as latex or other elastomeric polymer materials. Such elastic closure member(s) 60 are preferably passed through adjacent portions of myocardial tissue next to the opening 66 between the transmyocardial bloodflow passageway 10 and the lumen of the coronary blood vessel CBV (or secondary bloodflow passageway 12).

The elastic closure member(s) 60 is the elastically biased to a retracted state whereby the closure member(s) 60 will draw the adjacent portions of myocardium M together so as to close off the opening 66 between the transmyocardial bloodflow passageway 10 and the lumen of the coronary bloodflow CBV, as shown in FIG. 7b. Upon systolic contraction of the heart the relatively high pressures created within the left ventricle LV and transmyocardial bloodflow passageway 10 will cause the elastic closure member(s) 60 to stretch or expand, thereby forming opening 66 through which blood may flow from the transmyocardial bloodflow passageway 10 into the lumen of the coronary blood vessel CBV (or secondary bloodflow passageway 12) in the perfusion direction PD, as shown in FIG. 7a.

Thereafter, when the heart undergoes diastolic relaxation the relatively low filling pressures within the left ventricle LV and transmyocardial bloodflow passageway will allow the elastic closure member 60 to retract, thereby closing off the opening 66 and preventing blood from backflowing or regurgitating from the lumen of the coronary blood vessel CBV (or secondary bloodflow passageway 12) into the transmyocardial bloodflow passageway 10, in the backflow direction BD, as shown in FIG. 7b.

It will be appreciated that the elastic closure member 60 may be installed in any suitable method, such as by way of an appropriate suturing or stapling device which operates to attach the elastic closure member 60 at its desired location. Such installation of the elastic closure member 60 may be accomplished by open surgical technique or by way of catheter-based, transluminal methodology. For example, a catheter having a suturing or stapling device positioned therewithin may be advanced to a position adjacent the opening 66. Thereafter, negative pressure or other suitable drawings means may be utilized to draw adjacent segments of the myocardial tissue, from either side of the transmyocardial passageway 10, into the catheter. Thereafter, the desired elastic closure member 60 may be penetrated and threaded through the adjacent sides of the myocardial tissue so as to form the desired elastic closure member 60, as shown.

vii. Protrusive Stents and Stented Grafts for Stenting of the Transmyocardial Passageway In accordance with another aspect of the invention shown in FIGS. 8a–8c, protrusive stents or stented grafts may be positioned within the transmyocardial passageway 10, and may extend into one or more adjacent coronary vessels including a) an endogenous coronary vein, b) an endogenous coronary artery, c) a man-made passageway in the heart which connects to an endogenous coronary vein, d) a man-made passageway in the heart which connects to an endogenous coronary artery and/or e) a man-made passageway which extends between an endogenous coronary vein and an endogenous coronary artery. As described more fully herebelow, the protrusive stent apparatus 90, 90a, 90b of the present invention may incorporate one or more valving apparatus to intermittently block or direct bloodflow in accordance with various stages of the systolic/diastolic cardiac cycle. Furthermore, such protrusive stent apparatus may optionally be covered or juxtapositioned to a tubular graft or sheath so as to form a discrete tubular passageway.

Figure 8A:
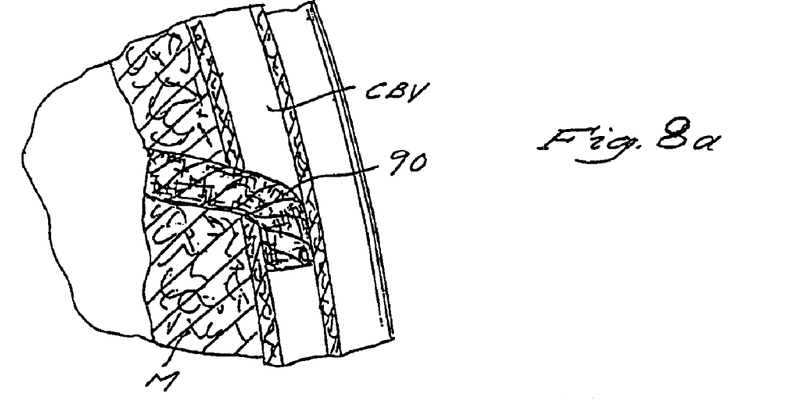
FIG. 8a is a longitudinal sectional view showing a protrusive stent apparatus of the present invention implanted within a transmyocardial passageway and extending into a coronary blood vessel (e.g., artery, vein or man-made passageway).

FIG. 8a shows a non-valved, non-covered protrusive stent apparatus 90 of the present invention positioned partially within a transmyocardial passageway 10, and extending into the coronary vessel CV (e.g., artery, vein or man-made passageway) to which such transmyocardial passageway 10 extends. As shown, the protrusive stent apparatus 90 is curved or bent at the junction of the transmyocardial passageway 10 and the coronary vessel CV, and preferably extends into the coronary vessel CV in the desired bloodflow direction.

The protrusive stent apparatus 90 may be formed of any suitable material, such as wire mesh or other metal or polymeric material, and may be self-expanding or pressure-expandable.

Figure 8B:
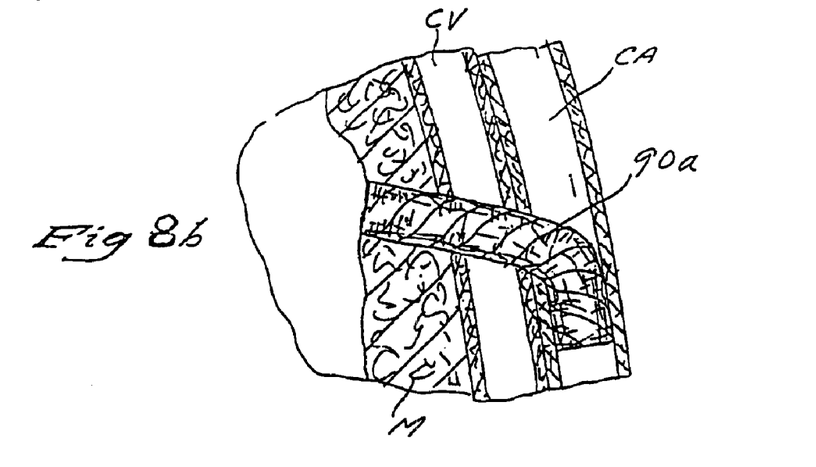

FIG. 8b shows a variant of the protrusive stent apparatus 90a positioned partially within a transmyocardial passageway 10, extending through a coronary vein CV, through a secondary passageway 12, and into a coronary artery CA. As shown the protrusive stent apparatus 90a is curved or bent at the junction of the secondary passageway 12 and the coronary artery CA and preferably extends into the coronary artery CA in the desired bloodflow direction.

Figure 8C:
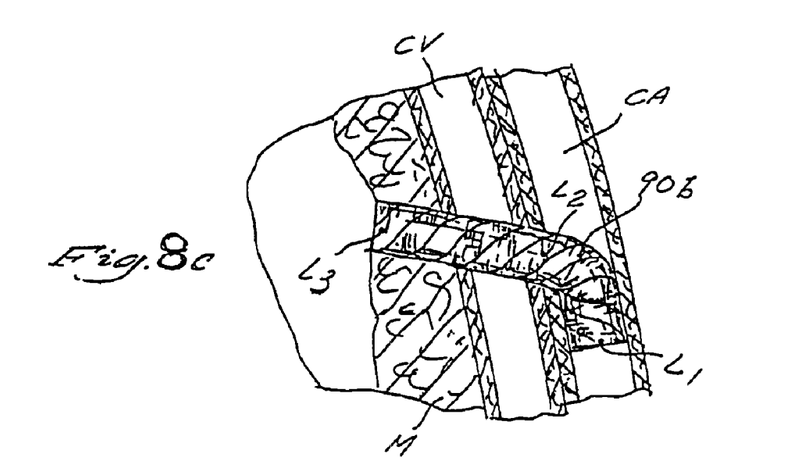
FIG. 8c is a longitudinal sectional view showing another alternative embodiment of the protrusive stent apparatus shown in FIG. 5a, having an optional tubular covering and/or optional valve(s) incorporated therein.

FIG. 8c shows alternative variations of the protrusive stent apparatus 90b wherein an optional tubular covering 92 is formed on the protrusive stent 90b. Such optional covering 92 may be any suitable tubular covering such as woven polyester or expanded, sintered polytetrafluoroethylene (PTFE). Additionally, or alternatively, one or more valves such as hinged occluder members or pliable elastomeric leaflets may be located within the protrusive stent apparatus 90b with or without covering 92, at locations $L_1$ and/or $L_2$ and/or $L_3$ to facilitate control and valving of bloodflow through the transmyocardial passageway 10, coronary vein CV, secondary passageway 12 and/or coronary artery CA. It will be appreciated that embodiments of the protrusive valving apparatus 90b which incorporates such valves at locations $L_1$ and/or $L_2$ and/or $L_3$ may be provided with appropriate openings or apertures in any covering 92 formed thereon to facilitate the desired inflow or outflow of blood at specific locations thereon.

These protrusive stent apparatus 90, 90a, 90b with or without the optional covering 92 and/or without the optional valves at locations $L_1$ and/or $L_2$ and/or $L_3$ offer advantages over previously known intramyocardial stents in that they do not require precise cutting to length or precise positioning within the myocardial passageway 10. Indeed, the protrusive stent apparatus 90, 90a, 90b of the present invention are intended to protrude into a coronary blood vessel CBV (e.g., artery, vein and/or man-made passageway) and the length of the portion of the stent apparatus 90, 90a, 90b which extends into such coronary blood vessel CBV is typically not critical. In this regard, there will exist no need for custom-fitting or precise precutting of the stent apparatus 90, 90a, 90b prior to implantation within the patient.

In embodiments where the stent apparatus 90, 90a, 90b is covered by a partial or complete tubular covering, such covering may be formed of any suitable material including but not necessarily limited to polyester, woven polyester, polytetrafluroethylene, expanded polytetraflouroethylene, polyurethane; silicone, polycarbonate, autologous tissue and, xenograft tissue.

The foregoing invention has been described hereabove with reference to certain presently preferred embodiments and examples only. No effort has been made to exhaustively describe all possible embodiments and examples in which the invention may be practiced. Indeed, various additions, deletions, modifications and alterations may be made to the above-described embodiments and examples without departing from the intended spirit and scope of the invention. Accordingly, it is intended that all such additions, deletions and modifications and alterations be included within the scope of the following claims.

What is claimed is:

1. A method for transmyocardial coronary revascularization, said method comprising the step of:
   1) creating a transmyocardial bloodflow passageway within the heart, said transmyocardial bloodflow passageway extending through the myocardium between a chamber of the heart and a coronary vein.

2. The method of claim 1 wherein said passageway is formed such that blood will flow from the chamber of the heart, through the transmyocardial bloodflow passageway, and through the lumen of the coronary vein, in a retrograde direction, so as to perfuse said region of the myocardium.

3. The method of claim 1 wherein said coronary vein is situated next to a coronary artery, and wherein said method further comprises the step of:
   2) forming a fistulous connection between said coronary vein and said adjacent coronary artery, at a location which is downstream of said transmyocardial bloodflow passageway, through said vein, through said fistulous connection, and into the adjacent coronary artery so as to provide enhanced bloodflow through said coronary artery.

4. The method of claim 3 wherein said fistulous connection is a secondary bloodflow passageway which extends from said coronary vein to said coronary artery.

5. The method of claim 1, further comprising the additional step of:
   3) blocking the lumen of the coronary vein at a location which is upstream of said transmyocardial bloodflow passageway.

6. The method of claim 3 wherein said method further comprises the steps of:
   blocking the lumen of the coronary vein at a location downstream of said fistulous connection.

7. The method of claim 1 further comprising the step of:
   b) placing an intraluminal valving apparatus within the lumen of the coronary vein, said intraluminal valving apparatus comprising at least one occluder member which is alternately deployable in:
      i) an open position whereby bloodflow is permitted to pass through the transmyocardial bloodflow passageway in a first direction; and,
      ii) a closed position whereby blood is prevented from backflowing through said transmyocardial bloodflow passageway, in a backflow direction.

8. The method of claim 7 wherein said transmyocardial bloodflow passageway is intended to provide a flow of blood from the chamber of the heart into said coronary vein, and wherein said first direction is the direction extending from said chamber of the heart to said coronary vein, and wherein said second direction is the direction extending from said coronary vein to the chamber of the heart.

9. The method of claim 7 wherein said transmyocardial bloodflow passageway is intended to drain blood from the coronary vein into the chamber of the heart, and wherein said first direction is the direction extending from the coronary vein to the chamber of the heart, and said second direction is the direction extending from the chamber of the heart to the coronary vein.

10. The method of claim 7 wherein the intravascular valving apparatus provided in step B is positioned downstream of the transmyocardial bloodflow passageway, and wherein said method further comprises the step of:
   4) blocking the lumen of the coronary vein upstream of the transmyocardial bloodflow passageway.

11. The method of claim 7 wherein the intravascualar valving apparatus provided in step B is portioned downstream of the transmyocardial bloodflow passageway, and wherein said method further comprises the step of:
   5) placing a second intravascular valving apparatus within the lumen of the coronary vein, upstream of said transmyocardial bloodflow passageway.

12. The method of claim 1 further comprising the step of:
   6) forming an endogenous tissue valve which is alternately moveable between:
      1) an open position whereby bloodflow is permitted to pass from said transmyocardial bloodflow passageway and through the lumen of said coronary vein, in a perfusion direction; and,
      2) a closed position whereby said tissue valve will prevent blood from flowing from the coronary vein into said transmyocardial bloodflow passageway, in a backflow direction.

13. The method of claim 12 wherein said tissue valve is formed at the junction of the transmyocardial bloodflow passageway and the coronary vein.

14. The method of claim 13 wherein the tissue valve comprises at least one segment of the coronary vein in combination with at least one underlying segment of myocardial tissue.

15. The method of claim 14 wherein at least one segment of coronary vein and the at least one segment of underlying tapered segment of myocardial tissue which form said tissue valve are sized and configured such that, when systolic blood pressure is created within said transmyocardial bloodflow passageway, said tissue valve will move to its open position, and thereafter when diastolic blood pressure is present in said transmyocardial bloodflow passageway, said tissue valve will move to its closed position.

16. The method of claim 1 further comprising the step of:
   connecting an elastic closure member to cardiac tissue on either side of said transmyocardial bloodflow passageway, said elastic closure member being alternately transitionable between:
      3) a stretched configuration whereby said transmyocardial bloodflow passageway is opened to permit blood to flow said transmyocardial bloodflow passageway into said coronary vein; and
      4) a retracted configuration whereby said transmyocardial bloodflow passageway is substantially blocked so as to prevent blood from backflowing from said coronary vein into said transmyocardial bloodflow passageway.

17. The method of claim 16 wherein said elastic closure member comprises a suture which is formed of elastic material, said suture being threaded through said myocardial tissue on opposite sides of said transmyocardial bloodflow passageway.

18. The method of claim 1 further comprising the step of:
   7) placing an intracardiac valving apparatus within the chamber of the heart, adjacent one end of said transmyocardial bloodflow passageway, said intracardiac valving apparatus being alternately deployable in:
      1) an open position whereby bloodflow is permitted to pass through the transmyocardial bloodflow passageway in a first direction; and,
      2) a closed position whereby through the transmyocardial bloodflow passageway, in a second direction, said second direction being opposite said first direction.

19. The method of claim 18 wherein said transmyocardial bloodflow passageway is intended to provide a flow of blood from the chamber of the heart to the coronary vein, and wherein said first direction is the direction extending from the chamber of the heart to the coronary vein, and said second direction is the direction extending from the coronary vein to the chamber of the heart.

20. The method of claim 18 wherein said transmyocardial bloodflow passageway is intended to drain blood from the coronary vein into the chamber of the heart, and wherein said first direction is the direction extending from the coronary vein to the chamber of the heart, and said second direction is the direction extending from the chamber of the heart to the coronary vein.

21. The method of claim 18 wherein the intracardiac valving apparatus provided in step b is attached to the wall of the chamber of the heart, and is portioned over the opening formed in the chamber of the heart by said transmyocardial bloodflow passageway.

22. The method of claim 21 wherein said intracardiac valving apparatus is sutured to the wall of the chamber of the heart.

23. The method of claim 21 wherein said intracardiac valving apparatus is adhered to the wall of the chamber of the heart.

24. The method of claim 1 further comprising the step of:
   8) placing a protrusive stent within said transmyocardial passageway, such that said protrusive stent extends into said coronary vein.

25. The method of claim 24 wherein said protrusive stent is uncovered.

26. The method of claim 24 wherein said protrusive stent is at least partially covered.

27. The method of claim 24 wherein said protrusive stent incorporates at least one valve to intermittently block blood flow, in at least one direction, through said transmyocardial passageway.

28. The method of claim 27 wherein said valve is operative to permit blood to flow from said chamber of the heart through said transmyocardial passageway, and into said coronary vein, but will prevent blood from backflowing from said coronary vein into said transmyocardial passageway.

* * * * *